United States Patent
Lemoine et al.

(10) Patent No.: US 8,597,622 B2
(45) Date of Patent: Dec. 3, 2013

(54) DEODORANT COSMETIC COMPOSITION COMPRISING A COMBINATION OF A LIPOPHILIC SALICYLIC ACID DERIVATIVE AND AN ANTIPERSPIRANT ALUMINIUM SALT

(75) Inventors: Cyril Lemoine, Saint-Cyr l'Ecole (FR); Emmanuelle Lebon-Hipolite, Abbecourt (FR)

(73) Assignee: L'Oreal, Paris (FR)

( * ) Notice: Subject to any disclaimer, the term of this patent is extended or adjusted under 35 U.S.C. 154(b) by 1027 days.

(21) Appl. No.: 11/918,741

(22) PCT Filed: Mar. 15, 2006

(86) PCT No.: PCT/EP2006/003303
§ 371 (c)(1),
(2), (4) Date: Feb. 7, 2008

(87) PCT Pub. No.: WO2006/111298
PCT Pub. Date: Oct. 26, 2006

(65) Prior Publication Data
US 2009/0035245 A1    Feb. 5, 2009

Related U.S. Application Data

(60) Provisional application No. 60/675,868, filed on Apr. 29, 2005.

(30) Foreign Application Priority Data

Apr. 19, 2005    (FR) ..................................... 05 50993

(51) Int. Cl.
*A61K 8/26* (2006.01)
*A61K 8/58* (2006.01)
*A61Q 15/00* (2006.01)

(52) U.S. Cl.
USPC .............................. 424/68; 424/400; 424/401

(58) Field of Classification Search
USPC .......................................... 424/400, 401, 68
See application file for complete search history.

(56) References Cited

U.S. PATENT DOCUMENTS

| | | | |
|---|---|---|---|
| 3,792,068 A | | 2/1974 | Luedders et al. |
| 4,526,780 A | * | 7/1985 | Marschner et al. ............. 424/66 |
| 4,767,750 A | | 8/1988 | Jacquet et al. |
| 4,822,596 A | | 4/1989 | Callingham et al. |
| 4,904,463 A | | 2/1990 | Johnson et al. |
| 5,001,156 A | | 3/1991 | Philippe et al. |
| 5,137,923 A | | 8/1992 | Philippe et al. |
| 5,143,718 A | | 9/1992 | Bar-Shalom |
| 5,262,407 A | | 11/1993 | Leveque et al. |
| 5,558,871 A | | 9/1996 | Griat et al. |
| 5,580,549 A | | 12/1996 | Fukuda et al. |
| 5,667,789 A | | 9/1997 | Collin et al. |
| 5,788,956 A | | 8/1998 | De Lacharriere et al. |
| 6,159,479 A | | 12/2000 | Pinzon |
| 2005/0019288 A1 | * | 1/2005 | Lemoine .......................... 424/67 |

FOREIGN PATENT DOCUMENTS

| | | |
|---|---|---|
| EP | 0 378 936 B1 | 7/1990 |
| EP | 0 570 230 B1 | 11/1993 |
| EP | 1 428 520 A2 | 6/2004 |
| EP | 1 486 199 A1 | 12/2004 |
| FR | 2 581 542 A1 | 11/1986 |
| FR | 2 607 498 A1 | 6/1988 |
| WO | WO 97/15278 | 5/1997 |
| WO | WO 97/44010 | 11/1997 |
| WO | WO 03/030853 A1 | 4/2003 |
| WO | WO 2004/073745 A1 | 9/2004 |

OTHER PUBLICATIONS

International Search Report for PCT/EP2006/003303, dated Jul. 11, 2006.
Charles Fox, "An Introduction to Multiple Emulsions," Cosmetics & Toiletries, Creams & Lotions Documentary, vol. 101, pp. 101-112 (1986).

* cited by examiner

*Primary Examiner* — Mina Haghighatian
*Assistant Examiner* — Luke Karpinski
(74) *Attorney, Agent, or Firm* — Novak Druce Connolly Bove + Quigg LLP

(57) ABSTRACT

The present invention relates to a deodorant cosmetic composition comprising: (a) at least one lipophilic salicylic acid derivative of formula (I) below, or a salt thereof: (b) at least one antiperspirant aluminum salt; in an (a)/(b) weight ratio of less than 1/20. The invention also relates to a cosmetic process for treating human perspiration and human body odor, in particular underarm perspiration and underarm odor, using this composition. The invention relates to the use of a combination of at least (a) one lipophilic salicylic acid derivative of formula (I), or a salt thereof, and of at least (b) one antiperspirant aluminum salt, in an (a)/(b) weight ratio of less than 1/20, as a deodorant active agent in a cosmetic composition.

28 Claims, No Drawings

DEODORANT COSMETIC COMPOSITION COMPRISING A COMBINATION OF A LIPOPHILIC SALICYLIC ACID DERIVATIVE AND AN ANTIPERSPIRANT ALUMINIUM SALT

CROSS REFERENCE TO RELATED APPLICATIONS

This application is a national phase application based on PCT/EP2006/003303, filed on Mar. 15, 2006, and claims the benefit of U.S. Provisional Application No. 60/675,868, filed on Apr. 29, 2005, and the priority of French Patent Application No. 0550993, filed Apr. 19, 2005, all of which are incorporated herein by reference in their entirety.

The invention relates to a deodorant cosmetic composition comprising (a) at least one lipophilic salicylic acid derivative or a salt thereof and (b) at least one antiperspirant aluminium salt in an (a)/(b) weight ratio of less than 1/20, preferably less than 1/25 and even more preferentially less than 1/50.

The invention also relates to a cosmetic process for treating human perspiration and human body odour using this composition.

Eccrine or apocrine sweat has little odour when it is secreted. It is the degradation of this sweat by bacteria via enzymatic reactions that produces malodorous compounds. The function of deodorant active agents is to reduce or prevent the formation of unpleasant odours. The various systems proposed to date may be grouped in major families.

(i) Bactericidal Substances or Substances that Limit Bacterial Growth:

There are bactericidal substances that destroy the resident bacterial flora. Among these substances, the one most widely used is Triclosan (2,4,4'-trichloro-2'-hydroxydiphenyl ether), which has the drawback of substantially modifying the ecology of the cutaneous flora. There are substances that reduce bacterial growth. Among these substances, mention may be made of transition-metal-chelating agents, for instance EDTA or DPTA. These materials deprive the medium of the metals required for the growth of the bacteria. These active agents are, unfortunately, potentially ecotoxic.

(ii) Substances that Block the Enzymatic Reactions Responsible for the Formation of Odoriferous Compounds:

Particular examples that may be mentioned include arylsulfatase inhibitors, 5-lipoxygenase inhibitors, aminocyclase inhibitors and β-glucuronidase inhibitors. Unfortunately, these inhibitors are often specific and thus of relatively poor efficacy compared with antibacterial agents.

(iii) Unpleasant-Odour Absorbers:

These odour absorbers "capture" or reduce the volatility of odoriferous compounds. Odour absorbers that may be mentioned include zeolites and cyclodextrins. These compounds are difficult to formulate since the compounds of the formula may interact and reduce their efficacy. Furthermore, the absorption is often selective, which limits the efficacy of these compositions.

Eccrine sweat is secreted to enable thermolysis during body heat disequilibria caused by effort or external heat. This sweat is responsible for the sensations of moisture and for the ring stains on clothing. Antiperspirant products were developed to avoid these unpleasant phenomena.

Several types of antiperspirant active agent exist:

(a) Moisture Absorbers:

The object of moisture absorbers is to capture sweat at the surface of the skin. Perspiration takes place, but the unpleasant phenomena associated therewith are avoided (panty liner principle). The moisture absorbers known in the prior art that may be mentioned include superabsorbent polymers of starch type grafted with homopolymers and copolymers of a sodium salt of poly(2-propenamide-co-propenoic acid) as described in patent application WO 03/030 853.

(b) Film-Forming Agents:

The principle of film-forming agents is to form a film at the surface of the skin that is sufficiently uniform to partially block the sweat ducts and thus prevent the sweat from being secreted.

(c) Aluminium Salts:

These active agents are the ones most commonly used as antiperspirant active agents. The principle of action of these active agents is to form a gel in the sweat duct. This gel creates a plug that partially blocks the sweat pores. The flow of sweat is thus reduced. These aluminium salts also have intrinsic efficacy since they are antibacterial. They thus also have a direct role on the deodorant efficacy by reducing the number of bacteria responsible for the degradation of sweat.

With the aim of obtaining long-term efficacy, there is a need to find better combinations of active agents.

The combination of a lipophilic salicylic acid derivative with an antiperspirant active agent is suggested in patent application WO 97/15278, which describes the cosmetic use of a substance P antagonist as an antiperspirant agent and the possibility of adding as a lipophilic additive a lipophilic salicylic acid derivative into these antiperspirant formulations.

The combination of a lipophilic salicylic acid derivative with an antiperspirant active agent has also been mentioned in patent application WO 04/073 745. The said document describes the efficacy-boosting effect of these lipophilic salicylic acid derivatives on 48 types of cosmetic active agent, among which are mentioned, without specifying their nature, antiperspirant active agents.

Among antiperspirant active agents, aluminium salts are cosmetic active agents that are generally used in contents of greater than 5% and preferably 20%. The Applicant has found that the addition of lipophilic salicylic acid derivatives as described in document WO 04/073 745 into antiperspirant compositions based on aluminium salts could disrupt the stability of these formulations and in particular strongly colour the products obtained, making them unsuitable for use.

The Applicant has discovered, surprisingly and unexpectedly, that a deodorant product with long-term efficacy, which is stable on storage and which does not colour, may be obtained by combining (a) at least one particular lipophilic salicylic acid derivative of formula (I) as defined later with (b) at least one antiperspirant aluminium salt in an (a)/(b) weight ratio of less than 1/20, preferably less than 1/25 and even more preferentially less than 1/50. Specifically, the combination of active agents used in a ratio of greater than 1/25 could destabilize the formulation containing them and/or produce a pink colour that the user doesn't want.

One subject of the present invention is thus a deodorant cosmetic composition comprising: (a) at least one lipophilic salicylic acid derivative of formula (I) as defined below, or a salt thereof, and (b) at least one antiperspirant aluminium salt; in an (a)/(b) weight ratio of less than 1/20, preferably less than 1/25 and even more preferentially less than 1/50.

The invention also relates to a cosmetic process for treating human perspiration and human body odour, in particular underarm perspiration and underarm odour, using this composition.

The invention relates to the use of a combination of at least (a) one lipophilic salicylic acid derivative of formula (I), or a salt thereof, and of at least (b) one antiperspirant aluminium salt, in an (a)/(b) weight ratio of less than 1/20, preferably less than 1/25 and even more preferentially less than 1/50, as a deodorant active agent in a cosmetic composition.

For the purposes of the present invention, the term "deodorant composition" means any composition capable of reducing the flow of sweat or of masking, absorbing, improving and/or reducing the unpleasant odour resulting from the decomposition of human sweat by bacteria.

The term "antiperspirant aluminium salt" means any aluminium salt or complex that has the effect of reducing the flow of sweat.

The term "lipophilic salicylic acid derivative" means any derivative that is insoluble at 1% and 25° C. in water, in its acid form.

The lipophilic salicylic acid derivatives in accordance with the invention correspond to formula

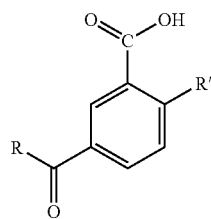

(I)

in which:
the radical R denotes a linear, branched or cyclic, saturated aliphatic chain containing from 2 to 22 carbon atoms; an unsaturated chain containing from 2 to 22 carbon atoms containing one or more double bonds that may be conjugated; an aromatic nucleus linked to the carbonyl radical directly or via saturated or unsaturated aliphatic chains containing from 2 to 7 carbon atoms; the said groups possibly being substituted with one or more substituents, which may be identical or different, chosen from (a) halogen atoms, (b) a trifluoromethyl group, (c) hydroxyl groups in free form or esterified with an acid containing from 1 to 6 carbon atoms, or (d) a carboxyl function in free form or esterified with a lower alcohol containing from 1 to 6 carbon atoms;
R' is a hydroxyl group or ester group of formula:

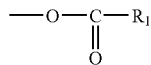

in which $R_1$ denotes a linear or branched, saturated or unsaturated aliphatic chain containing from 1 to 18 carbon atoms;
and also salts thereof derived from a mineral or organic base.

The lipophilic salicylic acid derivatives of formula (I) that may be used according to the invention are described in U.S. Pat. No. 6,159,479 and U.S. Pat. No. 5,558,871, FR 2 581 542, U.S. Pat. No. 4,767,750, EP 378 936, U.S. Pat. No. 5,267,407, U.S. Pat. No. 5,667,789, U.S. Pat. No. 5,580,549 and EP-A-570 230.

Preferentially, the radical R denotes a linear, branched or cyclic, saturated aliphatic chain containing from 3 to 11 carbon atoms; an unsaturated chain containing from 3 to 17 carbon atoms and comprising one or more conjugated or unconjugated double bonds; the said hydrocarbon-based chains possibly being substituted with one or more substituents, which may be identical or different, chosen from (a) halogen atoms, (b) a trifluoromethyl group, (c) hydroxyl groups in free form or esterified with an acid containing from 1 to 6 carbon atoms, or (d) a carboxyl function in free form or esterified with a lower alcohol containing from 1 to 6 carbon atoms;
R' is a hydroxyl group or ester group of formula:

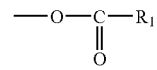

in which $R_1$ denotes a —O—(C═O)—$(CH_2)_n$—$CH_3$ radical in which n is a number ranging from 0 to 14;
and also salts thereof obtained by salification with a mineral or organic base.

The compounds that are more particularly preferred are those in which the radical R is a $C_3$-$C_{11}$ alkyl group and R' denotes hydroxyl.

Other compounds that are particularly advantageous are those in which R represents a chain derived from linoleic acid, linolenic acid or oleic acid.

Another group of compounds that are particularly preferred consists of compounds in which the radical R denotes a $C_3$-$C_{11}$ alkyl group bearing a carboxyl function in free form or esterified with a lower alcohol containing from 1 to 6 carbon atoms and R' denotes hydroxyl.

Among the compounds of formula (I) that are particularly preferred, mention may be made of: 5-n-octanoylsalicylic acid (or capryloylsalicylic acid); 5-n-decanoylsalicylic acid; 5-n-dodecanoyl-salicylic acid; 5-n-heptyloxysalicylic acid, and the corresponding salts thereof.

5-n-Octanoylsalicylic acid (or capryloyl-salicylic acid) manufactured under the trade name Mexoryl SAB by the company Chimex (see page 139 of the International Cosmetic Ingredient Dictionary, 6th edition, Volume 1, published by the review Cosmetic Toiletries and Fragrance Association, 1995) will be used more particularly.

The salts of the lipophilic salicylic acid derivatives of formula (I) may be obtained by salification with a mineral or organic base. Examples of mineral bases that may be mentioned include alkali metal or alkaline-earth metal hydroxides, for instance sodium hydroxide or potassium hydroxide, or aqueous ammonia.

Among the organic bases that may be mentioned are amines and alkanolamines. Quaternary salts, for instance those described in patent FR 2 607 498, are particularly advantageous.

The lipophilic salicylic acid derivatives of formula (I) that may be used according to the invention are described in U.S. Pat. No. 6,159,479 and U.S. Pat. No. 5,558,871, FR 2 581 542, FR 2 607 498, U.S. Pat. No. 4,767,750, EP 378-936, U.S. Pat. No. 5,267,407, U.S. Pat. No. 5,667,789, U.S. Pat. No. 5,580,549 and EP-A-570 230.

Among the compounds of formula (I) that are particularly preferred, mention may be made of: 5-n-octanoylsalicylic acid (or capryloylsalicylic acid); 5-n-decanoylsalicylic acid; 5-n-dodecanoylsalicylic acid; 5-n-heptyloxysalicylic acid, and the corresponding salts thereof.

5-n-Octanoylsalicylic acid (or capryloyl-salicylic acid) manufactured under the trade name Mexoryl SAB by the company Chimex (see page 139 of the International Cosmetic Ingredient Dictionary, 6th edition, Volume 1, published by the review Cosmetic Toiletries and Fragrance Association, 1995) will be used more particularly.

In the compositions of the invention, the concentration of salicylic compound of formula (I) preferably ranges from 0.001% to 20%, more preferentially from 0.01% to 15% and even more preferentially from 0.05% to 5% by weight relative to the total weight of the composition.

The aluminium salts in accordance with the invention are preferably chosen from aluminium halo-hydrates; aluminium zirconium halohydrates; and complexes of zirconium hydroxychloride and of aluminium hydroxychloride with an amino acid, such as those described in U.S. Pat. No. 3,792, 068, which are commonly known as "ZAG complexes".

Among the aluminium salts that may be mentioned in particular are aluminium chlorohydrate in activated or unactivated form, aluminium chlorohydrex, aluminium chlorohydrex polyethylene glycol complex, aluminium chlorohydrex propylene glycol complex, aluminium dichlorohydrate, aluminium dichlorohydrex polyethylene glycol complex, aluminium dichlorohydrex propylene glycol complex, aluminium sesquichlorohydrate, aluminium sesquichlorohydrex polyethylene glycol complex, aluminium sesquichlorohydrex propylene glycol complex, and aluminium sulfate buffered with sodium aluminium lactate.

Among the aluminium zirconium double salts that may be mentioned in particular are aluminium zirconium octachlorohydrate, aluminium zirconium pentachlorohydrate, aluminium zirconium tetrachlorohydrate and aluminium zirconium trichlorohydrate.

The complexes of zirconium hydroxychloride and of aluminium hydroxychloride with an amino acid are generally known under the name ZAG (when the amino acid is glycine). Among these products, mention may be made of the aluminium zirconium octachlorohydrex glycine, aluminium zirconium pentachlorohydrex glycine, aluminium zirconium tetrachlorohydrex glycine and aluminium zirconium trichlorohydrex glycine complexes.

Aluminium chlorohydrate in activated or unactivated form will be used more particularly.

The antiperspirant aluminium salts may be present in the composition according to the invention in a proportion of about from 0.5% to 25% by weight relative to the total weight of the composition.

The deodorant compositions according to the invention intended for cosmetic use may be in the form of lotions, creams or fluid gels distributed as an aerosol spray, in a pump-dispenser bottle or as a roll-on, in the form of thick creams distributed in tubes or a grille; in the form of wands (sticks), and may contain in this regard the ingredients generally used in products of this type and well known to those skilled in the art, provided that they do not interfere with the aluminium salt and the zinc salicylate described in the present invention.

The deodorant compositions according to the present invention intended for cosmetic use may comprise at least one aqueous phase. They are especially formulated as aqueous lotions or as water-in-oil, oil-in-water emulsions, or as multiple emulsions (oil-in-water-in-oil or water-in-oil-in-water triple emulsions (such emulsions are known and described, for example, by C. F. Fox in "Cosmetics and Toiletries", November 1986, Vol. 101, pages 101-112)).

The aqueous phase of the said compositions contains water and generally other water-soluble or water-miscible solvents. The water-soluble or water-miscible solvents include short-chain monoalcohols, for example of $C_1$-$C_4$, for instance ethanol or isopropanol; diols or polyols, for instance ethylene glycol, 1,2-propylene glycol, 1,3-butylene glycol, hexylene glycol, diethylene glycol, dipropylene glycol, 2-ethoxyethanol, diethylene glycol monomethyl ether, triethylene glycol monomethyl ether and sorbitol. Propylene glycol and glycerol will more particularly be used.

According to one particular form of the invention, the antiperspirant compositions may be anhydrous.

For the purposes of the invention, the term "anhydrous" refers to a composition whose content of free or added water is less than 3% and preferably whose content of added water is less than 1% by weight relative to the total weight of the composition.

The compositions according to the invention preferably comprise at least one water-immiscible organic liquid phase. This phase generally comprises one or more hydrophobic compounds that render the said phase water-immiscible. The said phase is liquid (in the absence of a structuring agent) at room temperature (20-25° C.). The water-immiscible organic liquid phase in accordance with the invention generally consists of an oil or a mixture of oils and comprises at least 80% of compounds with a vapour pressure not exceeding 4 kPa (30 mmHg) at 25° C.

The water-immiscible organic liquid phase preferably contains one or more volatile or non-volatile, silicone-based or hydrocarbon-based emollient oils. These emollient oils are especially described in U.S. Pat. No. 4,822,596 and U.S. Pat. No. 4,904,463.

Volatile silicones are defined, in a known manner, as being compounds that are volatile at room temperature. Mention may be made among these compounds of cyclic and linear volatile silicones of the dimethylsiloxane type whose chains comprise from 3 to 9 silicone-based residues. Cyclomethicones $D_4$, $D_5$ or $D_6$ are preferably chosen.

Non-volatile silicones are defined, in a known manner, as being compounds with a low vapour pressure at room temperature. The following are included among these compounds: polyalkylsiloxanes, in particular linear polyalkylsiloxanes, for instance the linear polydimethylsiloxanes, or dimethicones, sold by the company Dow Corning under the name "Dow Corning 245 Fluid"; polyalkylarylsiloxanes, for instance the polymethylphenylsiloxanes sold by the company Dow Corning under the name "Dow Corning 556 Fluid"; copolymers of polyether and siloxane, for instance dimethicone copolyols.

Among the non-volatile emollient oils that may be used in the present invention, examples that may be mentioned include: hydrocarbon-based derivatives, mineral oils, fatty alcohols, esters of $C_3$-$C_{18}$ alcohols with $C_3$-$C_{18}$ acids, esters of benzoic acid with $C_{12}$-$C_{18}$ alcohols and mixtures thereof, $C_2$-$C_6$ polyols preferably chosen from glycerol, propylene glycol or sorbitol, polyalkylene glycol polymers.

The emollient oils are preferably present in amounts ranging from 1% to 50% by weight and more preferably from 5% to 40% by weight relative to the total weight of the composition.

The deodorant cosmetic composition according to the invention may contain one or more additional deodorant active agents, for instance bacteriostatic agents or bactericidal agents such as 2,4,4'-trichloro-2'-hydroxydiphenyl ether (Triclosan), 2,4-dichloro-2'-hydroxydiphenyl ether, 3',4',5'-trichlorosalicylanilide, 1-(3',4'-dichlorophenyl)-3-(4'-chlorophenyl)urea (Triclocarban) or 3,7,11-trimethyl-dodeca-2,5,10-trienol (Farnesol); quaternary ammonium salts, for instance cetyltrimethylammonium salts or cetylpyridinium salts; chlorhexidine and salts; diglyceryl monocaprate, diglyceryl monolaurate or glyceryl monolaurate; polyhexamethylene biguanide salts.

In order to improve the homogeneity of the product, it is possible also to use one or more suspension agents preferably chosen from hydrophobic-modified montmorillonite clays, for instance hydrophobic-modified bentonites or hectorites. Examples that may be mentioned include the product stearalkonium bentonite (CTFA name) (product of reaction of bentonite and the quaternary ammonium stearalkonium chloride), such as the commercial product sold under the name Tixogel MP 250 by the company Sud Chemie Rheologicals, United Catalysts Inc. or the product disteardimonium hectorite (CTFA name) (product of reaction of hectorite and of distearyldimonium chloride) sold under the name Bentone 38 or Bentone Gel by the company Elementis Specialities.

The suspension agents are preferably present in amounts ranging from 0.1% to 5% by weight and more preferentially from 0.2% to 2% by weight relative to the total weight of the composition.

The compositions according to the invention may also contain at least one organic powder.

Among the fillers that may be used according to the invention, mention may be made of organic powders. In the present patent application, the term "organic powder" means any solid that is insoluble in the medium at room temperature (25° C.).

As organic powders that may be used in the composition of the invention, examples that may be mentioned include polyamide particles and especially those sold under the name Orgasol by the company Atochem; polyethylene powders; microspheres based on acrylic copolymers, such as those made of ethylene glycol dimethacrylate/lauryl methacrylate copolymer, sold by the company Dow Corning under the name Polytrap; polymethyl methacrylate microspheres, sold under the name Microsphere M-100 by the company Matsumoto or under the name Covabead LH85 by the company Wackherr; ethylene-acrylate copolymer powders, for instance those sold under the name Flobeads by the company Sumitomo Seika Chemicals; expanded powders such as hollow microspheres and especially microspheres formed from a terpolymer of vinylidene chloride, of acrylonitrile and of methacrylate and sold under the name Expancel by the company Kemanord Plast under the references 551 DE 12 (particle size of about 12 µm and density of 40 kg/m$^3$), 551 DE 20 (particle size of about 30 µm and a density of 65 kg/m$^3$) and 551 DE 50 (particle size of about 40 µm), or the microspheres sold under the name Micropearl F 80 ED by the company Matsumoto; powders of natural organic materials such as starch powders, especially of corn starch, wheat starch or rice starch, which may or may not be crosslinked, such as the starch powder crosslinked with octenylsuccinate anhydride, sold under the name Dry-Flo by the company National Starch; silicone resin microbeads such as those sold under the name Tospearl by the company Toshiba Silicone, especially Tospearl 240; amino acid powders such as the lauroyllysine powder sold under the name Amihope LL-11 by the company Ajinomoto; particles of wax microdispersion, which preferably have mean sizes of less than 1 µm and especially ranging from 0.02 µm to 1 µm, and which consist essentially of a wax or a mixture of waxes, such as the products sold under the name Aquacer by the company Byk Cera, and especially: Aquacer 520 (mixture of synthetic and natural waxes), Aquacer 514 or 513 (polyethylene wax), Aquacer 511 (polymer wax), or such as the products sold under the name Jonwax 120 by the company Johnson Polymer (mixture of polyethylene wax and paraffin wax) and under the name Ceraflour 961 by the company Byk Cera (micronized modified polyethylene wax); and mixtures thereof. The organic powder(s) may be present, for example, in an amount The cosmetic composition according to the invention may also comprise cosmetic adjuvants chosen from waxes, softeners, antioxidants, opacifiers, stabilizers, moisturizers, vitamins, fragrances, bactericides, preserving agents, polymers, fragrances, thickeners, propellants or any other ingredient usually used in cosmetics for this type of application.

Needless to say, a person skilled in the art will take care to select this or these optional additional compound(s) such that the advantageous properties intrinsically associated with the cosmetic composition in accordance with the invention are not, or are not substantially, adversely affected by the envisaged addition(s).

The waxes may be chosen from animal, fossil, plant, mineral and synthetic waxes. Mention may be made especially of beeswax, carnauba wax, candelilla wax, sugar cane wax, Japan wax, ozokerites, montan wax, microcrystalline waxes; paraffins and silicone waxes and resins.

The thickeners, which are preferably nonionic, may be chosen from modified or unmodified guar gums and celluloses, such as hydroxypropyl guar gum or cetylhydroxyethylcellulose, silicas, for instance Bentone Gel MIO sold by the company NL Industries, or Veegum Ultra sold by the company Polyplastic.

The amounts of these various constituents that may be present in the cosmetic composition according to the invention are those conventionally used in deodorant compositions.

The compositions according to the invention may also contain one or more other agents for structuring or gelling the water-immiscible organic liquid phase of the composition, such as linear solid fatty alcohols and/or waxes; fatty acids or salts thereof (stearic acid, sodium stearate or 12-hydroxystearic acid); dibenzylidene alditols (DBS); lanosterol, N-acylamino acid derivatives; di- or tricarboxylic acid derivatives, for instance alkyl-N,N'-dialkylsuccinamides (i.e.: dodecyl-N,N'-dibutylsuccinamide); elastomeric polyorganosiloxanes such as those described in patent application WO 97/44010.

The composition according to the invention may also be pressurized and may be packaged in an aerosol device.

A subject of the present invention is an aerosol device consisting of:
(A) a container comprising a deodorant composition as defined above,
(B) at least one propellant and a means for distributing the said aerosol composition.

The propellants generally used in products of this type, which are well known to those skilled in the art, are, for example, dimethyl ether (DME); volatile hydrocarbons such as n-butane, propane or isobutane, and mixtures thereof, optionally with at least one chlorohydrocarbon and/or fluorohydrocarbon; among the latter, mention may be made of the compounds sold by the company Dupont de Nemours under the names Freon® and Dymel®, and in particular monofluorotrichloromethane, difluorodichloromethane, tetrafluorodichloroethane and 1,1-difluoroethane sold especially under the trade name Dymel 152 A by the company Dupont. Carbon dioxide, nitrous oxide, nitrogen or compressed air may also be used as propellant.

The composition containing the deodorant active agent(s) and the propellant(s) may be in the same compartment or in different compartments in the aerosol container. According to the invention, the concentration of propellant generally ranges from 5% to 95% by pressurized weight and more preferably from 50% to 85% by weight relative to the total weight of the pressurized composition.

The distribution means, which forms a part of the aerosol device, generally consists of a distribution valve controlled by a distribution head, itself comprising a nozzle via which the aerosol composition is vaporized. The container containing the pressurized composition may be opaque or transparent. It may be made of glass, of polymeric material or of metal, optionally coated with a coat of protective varnish.

A subject of the present invention is also a cosmetic process for treating human underarm odours, which consists in applying to the underarm area an effective amount of a composition as defined above.

The examples that follow serve to illustrate the present invention. The amounts used in the compositions are expressed as weight percentages.

EXAMPLES 1 AND 2

Oil-In-Water Emulsions (Roll-On)

| Phase | Ingredients (INCI name) | Trade name | Example 1 | Example 2 (outside the invention) |
|---|---|---|---|---|
| A | Dimethicone | DC 200 350 cSt (Dow Corning) | 0.5 | 0.5 |
|   | Cetearyl alcohol | Nanol 1618F (Sasol) | 2.5 | 2.5 |
|   | Ceteareth-33 | Emuldac AS25 (Sasol) | 1.25 | 1.25 |
|   | PPG-15 stearyl ether | Arlamol E (Uniqema) | 3 | 3 |
|   | Propyl paraben | Nipasol M (Clariant) | 0.15 | 0.15 |
|   | Methyl paraben | Nipagin M (Clariant) | 0.2 | 0.2 |
|   | n-Octanoylsalicylic acid | Mexoryl SAB (Chimex) | 0.1 | 1 |
| B | Water |  | 62.3 | 61.4 |
| C | Aluminium chlorohydrate (50% aqueous solution) | Chlorhydrol 50% USP (Reheis) | 30 | 30 |
| Stability |  |  | White | Pink |
| Centrifugation 30 minutes at 4000 rpm |  |  | Stable | Slight phase separation |

Procedure:

Phases (A) and (B) are separately heated to 70° C. (A) and (B) are mixed together using a Turrax blender for 5 minutes and the mixture is then cooled to 55° C. with paddle stirring. (C) is added gently with stirring. The mixture is homogenized for 1 to 3 minutes. It is cooled to 35° C. with stirring.

Stability:

Stability conditions: 48 hours after manufacture, stored at room temperature.

It is found that Example 1 with a 1/150 weight ratio between the n-octanoylsalicylic acid and the aluminium salt is white. It is found that Example 2 (outside the invention) with a 1/15 weight ratio between the n-octanoylsalicylic acid and the aluminium salt is strongly pink and unacceptable for this type of product. Furthermore, the formula is not stable after centrifugation.

EXAMPLES 3 AND 4

Water-In-Oil Emulsions

| Phase | Ingredients | Trade name | Example 3 | Example 4 (outside the invention) |
|---|---|---|---|---|
| A | Isohexadecane | (BP) | 10.6 | 10.6 |
|   | Polyisobutylene containing esterified succinic end groups, diethylethanolamine salt | Chemcinnate 2000 (Chemron) | 1.9 | 1.9 |
|   | n-Octanoylsalicylic acid | Mexoryl SAB (Chimex) | 0.1 | 1 |
| B | Glycerol |  | 5 | 5 |
|   | Water |  | qs 100 | qs 100 |
|   | Aluminium chlorohydrate (50% aqueous solution) | Chlorhydrol 50% USP (Reheis) | 40 | 40 |
|   | Phenoxyethanol (and) methyl paraben (and) ethyl paraben (and) butyl paraben (and) isobutyl paraben (and) propyl paraben | Phenonip (NIPA) | 1 | 1 |
| Stability |  |  | Beige-coloured fluid | Thick pink paste |

Procedure:

The ingredients of phase A are weighed out in a beaker. The mixture is placed on a water bath to liquefy it a little. All of the water is weighed out in another beaker. Mechanical stirring is started. Next, the other constituents of phase B are added with stirring. The mixture is homogenized. The beaker of phase A is stirred with a Rayneri blender using a deflocculating paddle at a speed of 600 rpm. Phase B is added gently and slowly until a cream is obtained. The final stirring time should not exceed 10 minutes.

Stability:

Stability conditions: 48 hours after manufacture, stored at room temperature.

It is found that Example 3 with a 1/200 weight ratio between the n-octanoylsalicylic acid and the aluminium salt is white. It is found that Example 4 (outside the invention) with a 1/20 weight ratio between the n-octanoylsalicylic acid and the aluminium salt is strongly pink and unacceptable for this type of product. Furthermore, the formula is not stable after centrifugation.

EXAMPLES 5 TO 7

Aqueous-Alcoholic Roll-Ons

| Ingredients | Trade name | Example 5 | Example 6 | Example 7 (outside the invention) |
|---|---|---|---|---|
| Aluminium chlorohydrate (50% aqueous solution) | Chlorhydrol 50% USP (Reheis) | 20 | 20 | 20 |
| 96° Ethyl alcohol | | qs 100 | qs 100 | qs 100 |
| Water | | 14.9 | 14.9 | 14 |
| n-Octanoylsalicylic acid | Mexoryl SAB (Chimex) | 0.1 | 0.2 | 1 |
| Propylene glycol | | 5 | 5 | 5 |
| Hydroxypropylcellulose | Klucel MF Pharm (Aqualon) | 1 | 1 | 1 |
| Stability | | Clear, colourless | Clear, colourless | Clear, pink |

Procedure:

The hydroxypropylcellulose is thoroughly dispersed in the propylene glycol. The water and the aluminium salt are added. The mixture is homogenized. The alcohol and the n-octanoylsalicylic acid are then added. The resulting mixture is homogenized.

Stability:

Stability conditions: 48 hours after manufacture, stored at room temperature.

It is found that Examples 5 and 6 having, respectively, a 1/100 and a 1/50 weight ratio between the n-octanoylsalicylic acid and the aluminium salt are transparent and colourless. On the other hand, Example 7 (outside the invention) with a 1/10 weight ratio between the n-octanoylsalicylic acid and the aluminium salt is strongly pink and unacceptable for this type of product.

EXAMPLE 8

Stick

Antiperspirant Stick

| Ingredients | Trade name | Example 8 |
|---|---|---|
| Cyclopentasiloxane | 245 Fluid (Dow Corning) | qs 100 |
| PPG-14 butyl ether | Fluid AP (Amerchol) | 10 |
| Hydrogenated castor oil | Cutina HR Pulver (Cognis) | 4 |
| Aluminium chlorohydrate | Micro Dry Aluminium Chlorohydrate (Reheis) | 20 |
| n-Octanoylsalicylic acid | Mexoryl SAB (Chimex) | 0.1 |
| Stearyl alcohol | Lanette 18 (Cognis) | 14 |
| PEG-8 distearate | PEG-400 distearate (Stéarineries Dubois) | 2 |
| C12-15 Alkyl benzoate | C12/C15 benzoate (Stéarineries Dubois) | 15 |

Procedure:

The cyclopentasiloxane is heated to 65° C. The other ingredients are added (one by one) while remaining at 65-70° C. The mixture (transparent solution) is homogenized for 15 minutes. The two active agents are added. The resulting mixture is cooled to about 55° C. (a few degrees Celsius above the thickening point of the mixture) and is poured into sticks. The sticks are placed at 4° C. for 30 minutes.

The stick obtained is stable for 2 months at 45° C. and does not lead to any undesirable coloration.

The invention claimed is:

1. A deodorant cosmetic composition comprising (a) 5-n-octanoyl salicylic acid or at least one salt thereof; and (b) at least one antiperspirant aluminum salt; the weight ratio in the deodorant cosmetic composition of the 5-n-octanoyl salicylic acid to the aluminum salt being less than 1/50 and (a) and (b) being present in a deodorant effective amount and wherein the amount of the 5-n-octanoyl salicylic acid or at least one salt thereof is 0.001% to 0.5% relative to the total weight of the composition.

2. A composition, according to claim 1, wherein the at least one salt is obtained by salification with a mineral or organic base.

3. A composition according to claim 1, wherein the at least one antiperspirant aluminum salt is chosen from aluminum halohydrates, aluminum zirconium halohydrates, and complexes of zirconium hydroxychloride and of aluminum hydroxychloride with an amino acid.

4. A composition according to claim 3, wherein the at least one antiperspirant aluminum salt is chosen from aluminum chlorohydrate in activated or unactivated form, aluminum chlorohydrex, aluminum chlorohydrex polyethylene glycol complex, aluminum chlorohydrex propylene glycol complex, aluminum dichlorohydrate, aluminum dichlorohydrex polyethylene glycol complex, aluminum dichlorohydrex propylene glycol complex, aluminum sesquichlorohydrate, aluminum sesquichlorohydrex polyethylene glycol complex, aluminum sesquichlorohydrex propylene glycol complex, and aluminum sulfate buffered with sodium aluminum lactate.

5. A composition according to claim 3, wherein the at least one antiperspirant aluminum salt is chosen from aluminum zirconium octachlorohydrate, aluminum zirconium pentachlorohydrate, aluminum zirconium tetrachlorohydrate and aluminum zirconium trichlorohydrate.

6. A composition according to claim 3, wherein the
   at least one antiperspirant aluminum salt is chosen from
       complexes of zirconium hydroxychloride and of aluminum hydroxychloride with glycine.

7. A composition according to claim 6, wherein the
   at least one antiperspirant aluminum salt is chosen from
       aluminum zirconium octachlorohydrex glycine, aluminum zirconium pentachlorohydrex glycine, aluminum zirconium tetrachlorohydrex glycine, and aluminum zirconium trichlorohydrex glycine complexes.

8. A composition according to claim 1, wherein the
   at least one antiperspirant aluminum salt is aluminum chlorohydrate in activated or unactivated form.

9. A composition according to claim 1, wherein the
   at least one antiperspirant aluminum salt is present in an amount ranging from 0.5% to 25% by weight relative to the total weight of the composition.

10. A composition according to claim 1, wherein the composition is in the form chosen from:
   (a) lotions, creams, fluid gels, distributed as aerosol sprays, in pump-dispenser bottles, or as roll-ons;
   (b) creams and gels distributed in a tube or a grille;
   (c) and wands.

11. A composition according to claim 1, wherein the composition comprises at least one aqueous phase.

12. A composition according to claim 11, wherein the composition is in the form chosen from aqueous lotions, water-in-oil emulsions, oil-in-water emulsions, and multiple emulsions.

13. A composition according to claim 11, wherein the aqueous phase is comprised of water and one or more water-soluble or water-miscible solvents.

14. A composition according to claim 13, wherein the water-soluble or water-miscible solvents are chosen from $C_1$-$C_4$ monoalcohols, diols, and polyols.

15. A composition according claim 1, wherein the composition is anhydrous.

16. A composition according to claim 1, wherein the composition comprises at least one water-immiscible organic liquid phase.

17. A composition according to claim 16, wherein the at least one water-immiscible organic liquid phase comprises at least one volatile or non-volatile, silicone-based, or hydrocarbon-based emollient oil.

18. A composition according to claim 17, wherein the at least one emollient oil is present in an amount ranging from 1% to 50% by weight relative to the total weight of the composition.

19. A composition according to claim 17, wherein the at least one emollient oil is present in an amount ranging from 5% to 40% by weight relative to the total weight of the composition.

20. A composition according to claim 1, wherein the composition further comprises at least one additional deodorant active agent.

21. A composition according to claim 20, wherein the composition further comprises at least one bacteriostatic agent or bactericidal agent.

22. A composition according to claim 1, wherein the composition further comprises at least one suspension agent.

23. A composition according to claim 1, wherein the composition further comprises at least one organic powder.

24. A composition according to claim 1, wherein the composition further comprises at least one cosmetic additive chosen from waxes, softeners, antioxidants, opacifiers, stabilizers, moisturizers, vitamins, fragrances, bactericides, preserving agents, polymers, fragrances, thickeners, and propellants.

25. A composition according to claim 16, wherein the composition further comprises at least one agent for structuring or gelling the water-immiscible organic liquid phase.

26. An aerosol device comprising:
(A) a container comprising a deodorant cosmetic composition comprising: (a) 5-n-octanoyl salicylic acid or at least one salt thereof:
and (b) at least one antiperspirant aluminum salt; the weight ratio in the deodorant cosmetic composition of the compound of formula (I) to the aluminum salt being less than 1/50, and (a) and (b) being present in a deodorant effective amount and wherein the amount of the 5-n-octanoyl salicylic acid or at least one salt thereof is 0.001% to 0.5% relative to the total weight of the composition; and
(B) at least one aerosol propellant.

27. A method for treating
human body odor, comprising applying to the underarm area an effective amount of a deodorant cosmetic composition comprising:
(a) 5-n-octanoyl salicylic acid or at least one salt thereof; and
(b) at least one antiperspirant aluminum salt; the weight ratio in the deodorant cosmetic composition of the compound of formula (I) to the aluminum salt being less than 1/50, and (a) and (b) being present in a deodorant effective amount and wherein the amount of the 5-n-octanoyl salicylic acid or at least one salt thereof is 0.001% to 0.5% relative to the total weight of the composition.

28. A composition according to claim 1, wherein said aluminum salt is an aluminum halohydrate.

* * * * *